United States Patent
Kim et al.

(10) Patent No.: US 11,481,902 B2
(45) Date of Patent: Oct. 25, 2022

(54) DEVICE AND METHOD FOR DETECTING CEREBRAL MICROBLEEDS USING MAGNETIC RESONANCE IMAGES

(71) Applicant: Heuron Co., Ltd., Incheon (KR)

(72) Inventors: Dong Hyun Kim, Seoul (KR); Sang Hyeok Choi, Seoul (KR); Mohammed Al-Masni, Incheon (KR); Young Noh, Seoul (KR); Eung Yeop Kim, Incheon (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 17/374,250

(22) Filed: Jul. 13, 2021

(65) Prior Publication Data

US 2022/0020153 A1    Jan. 20, 2022

(30) Foreign Application Priority Data

Jul. 14, 2020  (KR) ..................... 10-2020-0086642

(51) Int. Cl.
*G06T 7/00* (2017.01)
*G16H 30/20* (2018.01)
(Continued)

(52) U.S. Cl.
CPC .......... *G06T 7/0014* (2013.01); *A61B 5/0042* (2013.01); *A61B 5/02042* (2013.01);
(Continued)

(58) Field of Classification Search
CPC ......... G06T 7/0014; G06T 2207/10088; G06T 2207/20076; G06T 2207/20081;
(Continued)

(56) References Cited

U.S. PATENT DOCUMENTS

2016/0170002 A1    6/2016  Park et al.

FOREIGN PATENT DOCUMENTS

CN        111374712 A     7/2020
JP         6746027 B1     8/2020
(Continued)

OTHER PUBLICATIONS

Liu et al. 2019 NeuroImage 198:271-282 (Year: 2019).*
(Continued)

*Primary Examiner* — Colin T. Sakamoto
*Assistant Examiner* — Patrick M Mehl
(74) *Attorney, Agent, or Firm* — Sughrue Mion, PLLC

(57) ABSTRACT

A device and method for detecting cerebral microbleeds use magnetic resonance images. The disclosed device includes a preprocessing unit that normalizes an SWI image and a phase image, respectively, of the magnetic resonance images, and performs phase image conversion for inverting a code of the normalized phase image, a YOLO neural network module that receives a two-channel image in which the preprocessed SWI image and phase image are concatenated and detects a plurality of candidate regions for the cerebral microbleeds, and a cerebral microbleeds determination neural network module that receives patch images of candidate regions of the SWI image and phase image based on the candidate regions and determines whether the patch images of each candidate region are an image with a symptom of the cerebral microbleeds through a neural network operation.

12 Claims, 7 Drawing Sheets

(51) Int. Cl.
  *G16H 50/20* (2018.01)
  *A61B 5/00* (2006.01)
  *A61B 5/02* (2006.01)
  *A61B 5/055* (2006.01)

(52) U.S. Cl.
  CPC ............ *A61B 5/055* (2013.01); *A61B 5/7267* (2013.01); *A61B 5/7485* (2013.01); *G16H 30/20* (2018.01); *G16H 50/20* (2018.01); *A61B 2576/026* (2013.01); *G06T 2207/10088* (2013.01); *G06T 2207/20076* (2013.01); *G06T 2207/20081* (2013.01); *G06T 2207/20084* (2013.01); *G06T 2207/30016* (2013.01)

(58) Field of Classification Search
  CPC . G06T 2207/20084; G06T 2207/30016; G06T 2207/30096; G06T 7/0012; A61B 5/0042; A61B 5/02042; A61B 5/055; A61B 5/7267; A61B 5/7485; A61B 2576/026; G16H 30/20; G16H 50/20
  See application file for complete search history.

(56) References Cited

FOREIGN PATENT DOCUMENTS

| KR | 2001-0086855 A | 9/2001 |
|---|---|---|
| KR | 10-2016-0071230 A | 6/2016 |
| KR | 10-1948701 B1 | 2/2019 |
| KR | 10-1995383 B1 | 7/2019 |
| KR | 10-2067412 B1 | 1/2020 |
| KR | 10-2056989 B1 | 2/2020 |
| KR | 10-2097738 B1 | 4/2020 |

OTHER PUBLICATIONS

Dou et al. 2016 IEEE Trans. Medical Imaging 35:1182-1195 (Year: 2016).*
Redmon et al. 2016 arXiv:1612.08242v1 9 pages (Year: 2016).*
Al-masni et al. 2020 42nd Annual International Conference of the IEEE Engineering in Medicine & Biology Society pp. 1055-1058 (Year: 2020).*
Al-masni et al. 2020 NeuroImage: Clinical 28: 102464 14 pages (Year: 2020).*
Korean Patent Office, Notice of Preliminary Rejection dated Sep. 9, 2021 in counterpart KR Application No. 10-2020-0086642.
Korean Patent Office, Decision for Grant of Patent dated Nov. 12, 2021 in counterpart KR Application No. 10-2020-0086642.
Yicheng Chen, "Development of Deep Learning Methods for Magnetic Resonance Phase Imaging of Neurological Disease", Dissertation for degree of Doctor of the University of California, 2019 (135 pages total).
Liu et al., "Cerebral microbleed detection using Susceptibility Weighted Imaging and deep learning", NeuroImage, No. 198, 2019, pp. 271-282 (12 pages total).

* cited by examiner

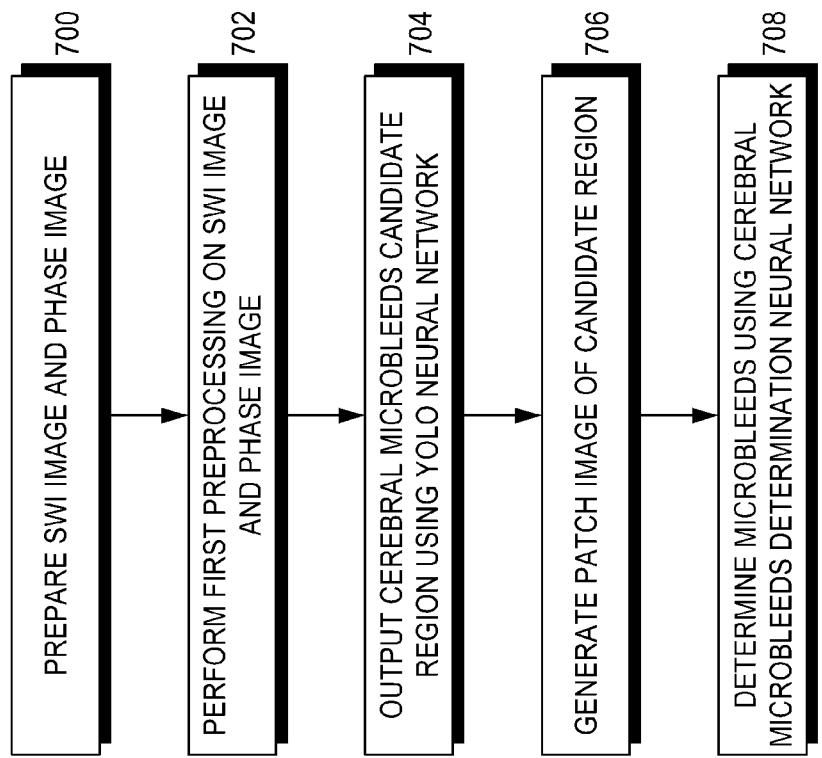

DEVICE AND METHOD FOR DETECTING CEREBRAL MICROBLEEDS USING MAGNETIC RESONANCE IMAGES

CROSS-REFERENCE TO RELATED APPLICATIONS

This application claims the priority of Korean Patent Application No. 10-2020-0086642 filed on Jul. 14, 2020, in the Korean Intellectual Property Office, the disclosure of which is incorporated herein by reference.

BACKGROUND

Field

The present disclosure relates to a device and method for detecting cerebral microbleeds, and more particularly, to a device and method for detecting cerebral microbleeds using magnetic resonance images and a neural network.

Description of the Related Art

Cerebral microbleeds (CMBs) are minor chronic cerebral hemorrhages that are considered diagnostic indicators of various cerebrovascular diseases such as stroke, dysfunction, dementia, and cognitive disorder. Cerebral microbleeds occur predominantly in several populations, including the healthy elderly, and have a high probability of causing intracranial bleeding and may be a biomarker for cerebral amyloid angiography and cerebral microvascular disease.

In addition, the cerebral microbleeds may increase clinical impact of ischemic stroke, traumatic brain injury, and Alzheimer's disease. In fact, as a result of direct pathological observation, it was found that the cerebral microbleeds inflict damage to surrounding brain tissue and cause dysfunction, dementia, and cognitive disorder.

Therefore, early detection of cerebral microbleeds and distinguishing the cerebral microbleeds from lime substances, iron and veins which can be mistaken for the cerebral microbleeds are very important tasks for diagnosis and treatment.

Conventionally, CT and magnetic resonance images have been used to detect cerebral microbleeds. Magnetic resonance images have been more preferred in detecting microbleeds compared to CT because they helped to distinguish between paramagnetic bleeding and diamagnetic lime substance.

In particular, a sensitivity-weighted imaging (SWI) image among magnetic resonance images has high discrimination power in cerebral microbleeds, but has a problem in that it takes a long time for a neurosurgeon to visually inspect the cerebral microbleeds, and it is difficult to successfully identify the cerebral microbleeds.

To improve the detection performance of the cerebral microbleeds, other experts or readers such as automated CAD have been used. However, it is still difficult to automatically detect the cerebral microbleeds since a change in a location of microbleeds inside the brain is large, a size of microbleeds is small, and similar substances such as a lime substance exist.

SUMMARY

An object of the present disclosure provides a method and device for detecting cerebral microbleeds with improved performance using an artificial neural network.

In addition, an object of the present disclosure provides a magnetic resonance image preprocessing method suitable for detecting cerebral microbleeds using an artificial neural network.

In order to achieve the above-described technical objects, a device for detecting cerebral microbleeds using magnetic resonance images includes: a preprocessing unit that normalizes an SWI image and a phase image, respectively, of the magnetic resonance images, and performs phase image conversion for inverting a code of the normalized phase image; a YOLO neural network module that receives a two-channel image in which the preprocessed SWI image and phase image are concatenated and detects a plurality of candidate regions for the cerebral microbleeds; and a cerebral microbleeds determination neural network module that receives patch images of candidate regions of the SWI image and phase image based on the plurality of candidate regions and determines whether the patch images of each candidate region are an image with a symptom of the cerebral microbleeds through a neural network operation.

The preprocessing unit may further perform preprocessing of calculating an average value of slice images adjacent to the normalized SWI image and the converted phase image, and reflecting the calculated average value.

The YOLO neural network module may be trained by backpropagating a loss with a ground truth (GT) image to output a plurality of bounding boxes and probability information of each bounding box.

The cerebral microbleeds determination neural network module may include a convolutional neural network (CNN) layer and a fully connected (FC) layer, and may be trained by backpropagating a loss with a ground truth (GT).

Each patch image of the candidate regions for the plurality of candidate regions may be generated using a candidate region of the SWI image in which normalization and an adjacent slice average operation have been performed, and a candidate region of the phase image in which the normalization and the adjacent slice average operation are reflected and a code inversion is not reflected.

The candidate region patch image may be a one-channel image in which a portion of the candidate region of the SWI image in which the normalization and the adjacent slice average operation are performed and a portion of the candidate region of the phase image in which the normalization and the adjacent slice average operation are performed are continuously connected.

In order to achieve the above-described technical objects, a method of detecting cerebral microbleeds using magnetic resonance images includes: (a) performing preprocessing that normalizes an SWI image and a phase image, respectively, of the magnetic resonance images, and performs phase image conversion for inverting a code of the normalized phase image; performing a YOLO neural network operation that receives a two-channel image in which the preprocessed SWI image and phase image are concatenated and detects a plurality of candidate regions for the cerebral microbleeds; and (c) performing a cerebral microbleeds determination neural network operation that receives patch images of candidate regions of the SWI image and phase image based on the plurality of candidate regions and determines whether the patch images of each candidate region are an image with a symptom of the cerebral microbleeds through a neural network operation.

According to the present disclosure, it is possible to detect cerebral microbleeds with improved performance through magnetic resonance image preprocessing suitable for detecting the cerebral microbleeds using an artificial neural network.

BRIEF DESCRIPTION OF THE DRAWINGS

The above and other aspects, features and other advantages of the present disclosure will be more clearly understood from the following detailed description taken in conjunction with the accompanying drawings, in which

FIG. 7 is a flowchart illustrating an overall flow of a method of determining cerebral microbleeds according to an embodiment of the present disclosure.

DETAILED DESCRIPTION OF THE PREFERRED EMBODIMENT

Figure 1:
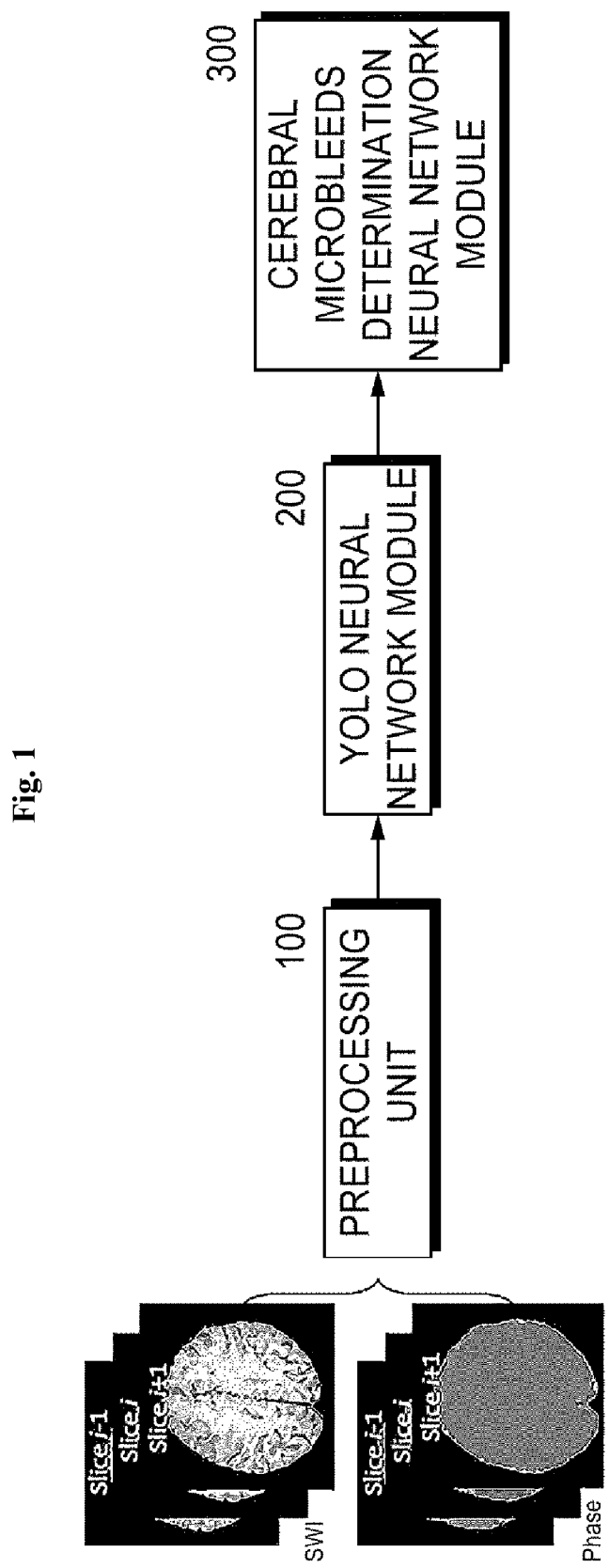
FIG. 1 is a diagram illustrating an overall structure of a device for detecting cerebral microbleeds using magnetic resonance images according to an embodiment of the present disclosure.

Hereinafter, the present disclosure will be described with reference to the accompanying drawings. However, the present disclosure may be implemented in various different forms, and is not limited to exemplary embodiments described herein.

In addition, in the drawings, portions unrelated to the description will be omitted to obviously describe the disclosure, and similar reference numerals are attached to similar portions throughout the specification.

Throughout the present specification, when any one part is referred to as being "connected to" another part, it means that any one part and another part are "directly connected to" each other or are "indirectly connected to" each other with the other part interposed therebetween.

In addition, unless explicitly described to the contrary, "including" any component will be understood to imply the inclusion of other components rather than the exclusion of other components.

Hereinafter, embodiments of the present disclosure will be described in detail with reference to the accompanying drawings.

FIG. 1 is a diagram illustrating an overall structure of a device for detecting cerebral microbleeds using magnetic resonance images according to an embodiment of the present disclosure.

Referring to FIG. 1, a device for detecting cerebral microbleeds using magnetic resonance images according to an embodiment of the present disclosure includes a preprocessing unit 100, a YOLO neural network module 200, and a cerebral microbleeds determination neural network module 300.

The device for detecting cerebral microbleeds according to the present disclosure detects whether the cerebral microbleeds have occurred from magnetic resonance images of a cerebral region, and a region where the cerebral microbleeds have occurred when the cerebral microbleeds have occurred.

Two types of magnetic resonance images are input to the device for detecting cerebral microbleeds according to the present disclosure. A first magnetic resonance image is a sensitivity-weighted imaging (SWI) image, and a second magnetic resonance image is a phase image. The SWI image is an image weighted by susceptibility, and is an image in which an image of the existing gradient-echo technique is changed to 3D spatial resolution and an image which sensitively reacts to compounds distorting a magnetic field. Such SWI images are useful for detecting blood substances, calcium, or the like.

The phase image is an image generated by extracting only a phase value from the magnetic resonance images acquired by a gradient echo method.

The conventional detection of cerebral microbleeds uses only the SWI image, but the present disclosure inputs both the SWI image and the phase image. The present disclosure detects cerebral microbleeds based on a neural network, and improves detection performance by allowing the information of the phase image to be used together for accurate determination in the neural network.

The SWI image and the phase image are acquired independently, the SWI image includes a plurality of slice images, and the phase image also includes a plurality of slice images. The device for detecting cerebral microbleeds of the present disclosure detects cerebral microbleeds for each slice image.

Hereinafter, the SWI image and the phase image input to the device for detecting cerebral microbleeds of the present disclosure refer to one slice image and do not refer to a set of slice images.

The preprocessing unit 100 receives the SWI image and the phase image, performs preprocessing on the SWI image and the phase image, and generates an image input to the YOLO neural network module 200. The preprocessing unit 100 is a key component of the present disclosure, and performs preprocessing on the SWI image and the phase image so that cerebral microbleeds are appropriately detected in the neural network. The detailed structure and preprocessing method of the preprocessing unit 100 will be described later with reference to FIG. 2.

The input image (an image in which the SWI image and the phase image are concatenated) preprocessed by the preprocessing unit 100 is input to the YOLO neural network module 200.

The YOLO neural network is a known neural network as one of the recently proposed convolutional neural network (CNN) techniques for detecting objects of interest. The device for detecting cerebral microbleeds of the present disclosure utilizes the YOLO neural network as one of the components thereof.

The YOLO neural network is a neural network designed to be suitable for detecting objects with a relatively small amount of computation, and is a neural network that is easy to calculate and optimize faster than the existing R-CNN. However, there is a problem that the YOLO neural network does not exhibit high performance for accurate object detection. For this reason, the YOLO neural network was not used for object detection of magnetic resonance images with low discrimination power.

The present disclosure does not use the YOLO neural network as a final means of detecting cerebral microbleeds, and in the present disclosure, the YOLO neural network module 200 functions to output a plurality of candidate regions. The YOLO neural network module 200 determines a number of regions with the possibility of cerebral microbleeds in the input image as candidate regions for cerebral microbleeds, and the YOLO neural network module 200 outputs only the candidate region but does not perform a final determination.

The input image generated through the preprocessing unit 100 is pre-processed so that the recommendation of the candidate region may be properly performed in the YOLO neural network module 200, and the YOLO neural network module 200 may be used for magnetic resonance images through the preprocessing suggested by the present disclosure.

The determination of whether the candidate region selected by the YOLO neural network module 200 is cerebral microbleeds is made by the cerebral microbleeds determination neural network module 300.

The cerebral microbleeds determination neural network module 300 receives the candidate region image selected by the YOLO neural network module 200 and finally determines whether the candidate region image input through the neural network operation is cerebral microbleeds.

According to the embodiment of the present disclosure, the cerebral microbleeds determination neural network module 300 may be implemented as a CNN-based neural network, but is not limited thereto.

When the candidate region is selected by the YOLO neural network module 200, a patch image of a candidate region, which is an image of a portion corresponding to the candidate region in the SWI image and the phase image, is input to the cerebral microbleeds determination neural network module 300. Patch images of each of the candidate regions are determined independently. For example, when five candidate regions are selected by the YOLO neural network module 200, the determination of whether patch images of the five candidate regions are an image reflecting cerebral microbleeds independently is made by the cerebral microbleeds determination neural network module 300.

At this time, the candidate region image input to the cerebral microbleeds determination neural network module 300 may be an image in which a candidate region is selected from the same image as the preprocessed image input to the YOLO neural network module 200, and may be an image in which a candidate region is selected after being preprocessed in a different manner from the image input to the YOLO neural network module 200. The preprocessing of the image input to the cerebral microbleeds determination neural network module 300 will be described with reference to FIG. 2.

Figure 2:
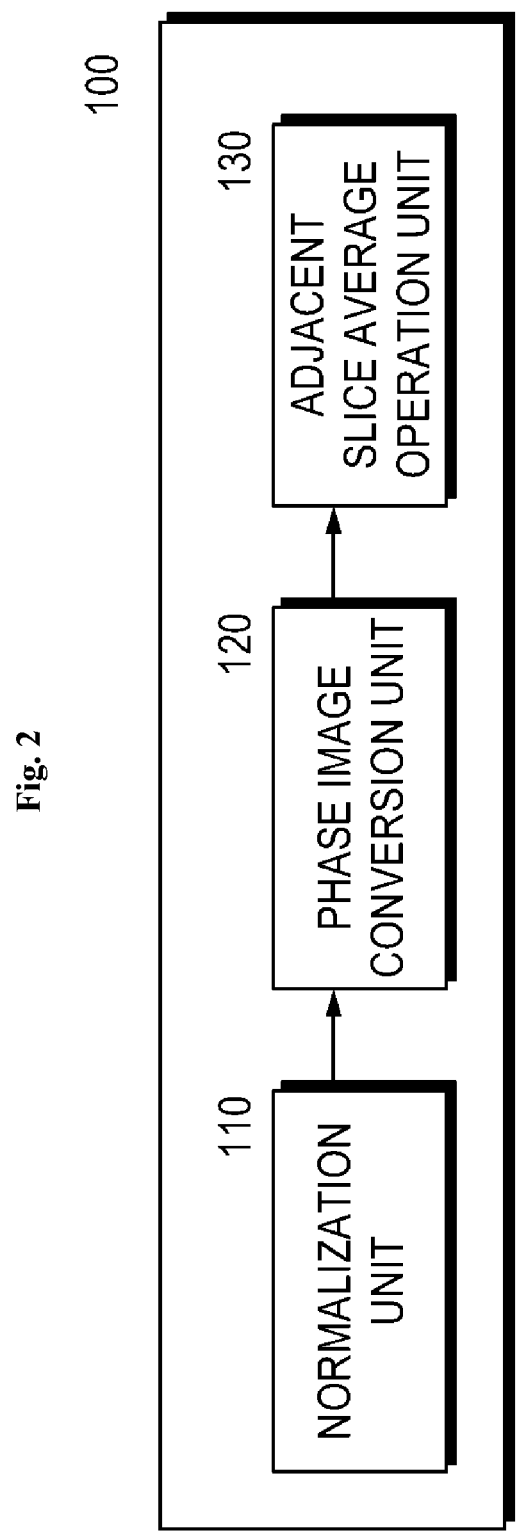
FIG. 2 is a block diagram illustrating a configuration of a preprocessing unit in the device for detecting cerebral microbleeds according to an embodiment of the present disclosure.

FIG. 2 is a block diagram illustrating a configuration of the preprocessing unit in the device for detecting cerebral microbleeds according to the embodiment of the present disclosure.

Referring to FIG. 2, the preprocessing unit according to the embodiment of the present disclosure includes a normalization unit 110, a phase image conversion unit 120, and an adjacent slice average operation unit 130.

The normalization unit 110 performs normalization on the SWI image and the phase image so that the SWI image and the phase image have only a predetermined range of values.

The normalization unit 110 performs the normalization on each of the SWI image and the phase image. For example, the normalization unit may perform the normalization on the SWI image and the phase image so that the SWI image and the phase image have a pixel value between 0 and 1.

According to the embodiment of the present disclosure, a normalization operation may be performed so that the SWI image and the phase image have values of 0 to 1 as shown in Equation 1 below.

$I_{norm}$=Pixel value of each image−Image minimum value/Image maximum value−Image minimum value [Equation 1]

The phase image conversion unit 120 converts the normalized phase image. According to the preferred embodiment of the present disclosure, the phase image conversion unit 120 converts the normalized phase image as shown in Equation 2 below.

Converted phase image=1−(normalized phase image) [Equation 2]

As will be described later, the SWI image and the phase image are concatenated to be input to form two channels. When the two channel values are added, the candidate region detection performance of the YOLO neural network module may be degraded. In the magnetic resonance images, a low-intensity point of the SWI image corresponds to a low-intensity point of the phase image. For this reason, when the values of the two images are added at the corresponding point, feature values of the image are canceled, making it difficult to accurately identify.

For this reason, the preprocessing unit 100 of the present disclosure inverts a code of the normalized phase image through the phase image conversion unit 120, and thus, prevents the features from being cancelled when the values of the phase image and the SWI image are added.

The adjacent slice average operation unit 130 generates the image reflecting the average value of the adjacent SWI image and phase image. For example, when a target slice is an N-th slice image, an average of an (N−1)-th slice image, an (N+1)-th slice image, and an N-th slice image is operated. Here, the targets of the average operation are SWI slice images that have been normalized and phase slice images that have undergone the phase image conversion. As described above, the SWI image and the phase image are composed of a plurality of slices, and the detection of cerebral microbleeds of the present disclosure is performed in units of slice images.

That is, the slice average operation is performed at the last stage of the preprocessing, and the slice average operation is performed to determine cerebral microbleeds by reflecting information of adjacent slices together.

Figure 3:
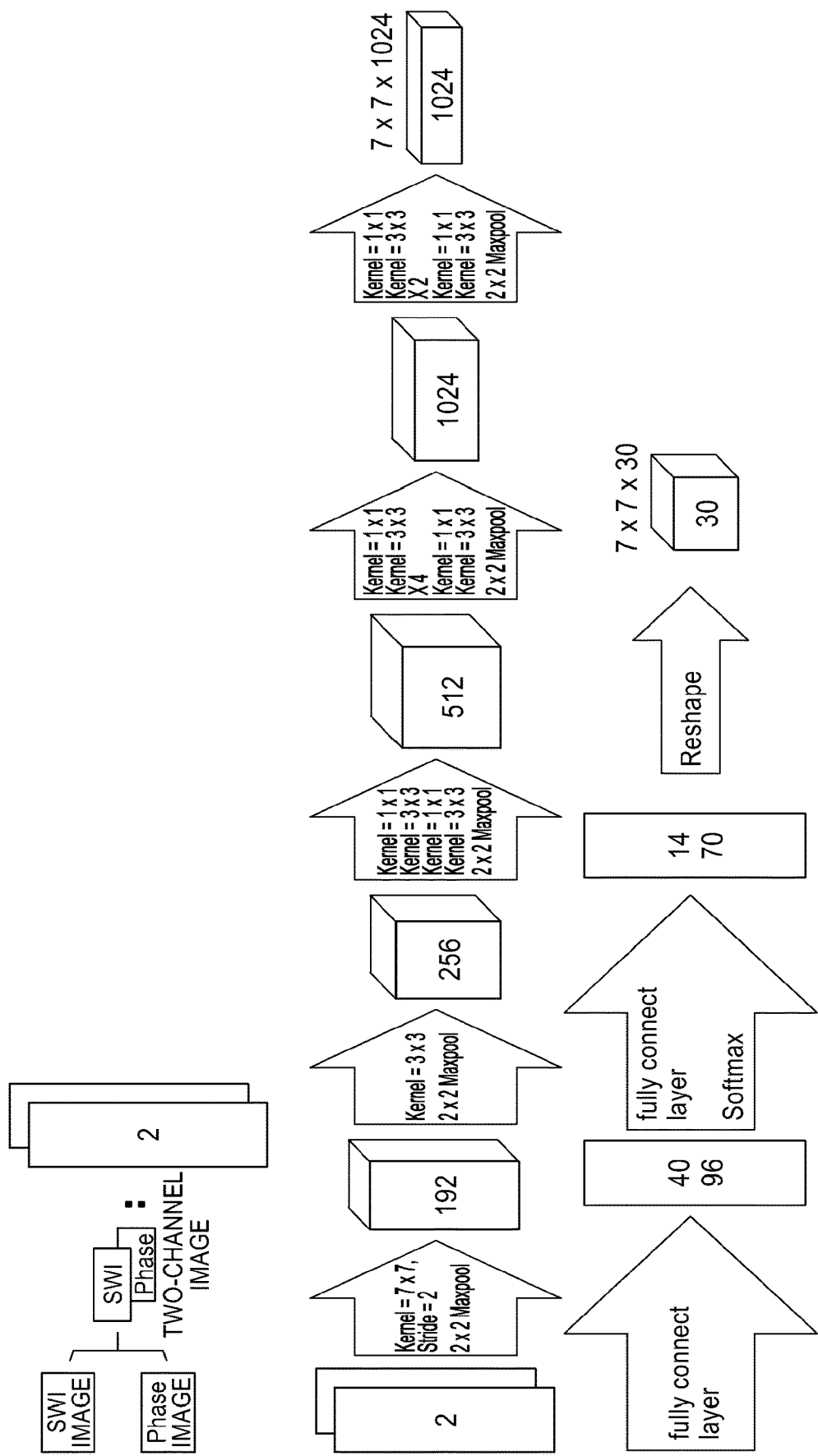
FIG. 3 is a diagram illustrating a structure of a YOLO neural network module according to an embodiment of the present disclosure.

FIG. 3 is a diagram illustrating a structure of the YOLO neural network module according to the embodiment of the present disclosure.

The image in which the SWI image and the phase image preprocessed by the preprocessing unit 100 are concatenated is input to the YOLO neural network module 200. Since the two images are concatenated, it may be defined as a two-channel image.

The YOLO neural network module 200 performs a convolution operation on a plurality of layers, and FIG. 3 illustrates a case in which the convolution operation is performed through a total of four layers. Of course, the number of layers illustrated in FIG. 3 is exemplary, and the number of convolution layers may be changed, as necessary.

Each time the convolution operation is performed in each layer, the size of the image is reduced by maxpooling, and the number of channels of the image increases. FIG. 3 shows a case in which the number of channels of the image increases in the order of 2, 192, 256, 512, and 1024.

When the convolution operation in the convolution layer is completed, it passes through two fully connected (FC) layers, and finally, 7×7×30 data is output. Of course, it will be apparent to those skilled in the art that the size and number of channels of each layer illustrated in FIG. 3 are also exemplary and can be changed, as necessary.

The YOLO neural network module may be trained by supervised learning using ground truth (GT). As the ground truth, the magnetic resonance images in which the cerebral microbleeds exist in some regions may be used.

When the training is performed using the GT, the difference between the output of the YOLO neural network module and the GT image is set as a loss, and the weight of the convolution kernel of each layer is trained while backpropagating the loss. Since the training structure of the convolutional neural network is a widely known technology, a detailed description thereof will be omitted.

Figure 4:
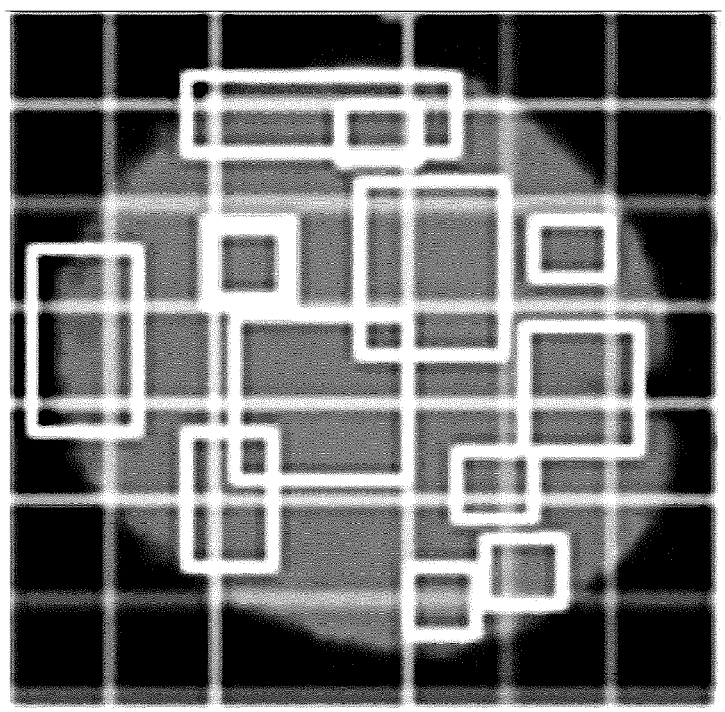
FIG. 4 is a diagram illustrating an example of an image output from the YOLO neural network module according to the embodiment of the present disclosure.

FIG. 4 is a diagram illustrating an example of an image output from the YOLO neural network module according to the embodiment of the present disclosure.

Referring to FIG. 4, the YOLO neural network module outputs an image in which a plurality of bounding boxes is formed. As illustrated in the present disclosure, when the YOLO neural network module is trained to detect cerebral microbleeds, the YOLO neural network module outputs an image in which a bounding box is formed in the region where the cerebral microbleeds are likely to occur.

The image output from the YOLO neural network module includes the bounding box and probability information of each bounding box. Here, the probability information means a probability that the bounding box region is the cerebral microbleeds.

Figure 5:
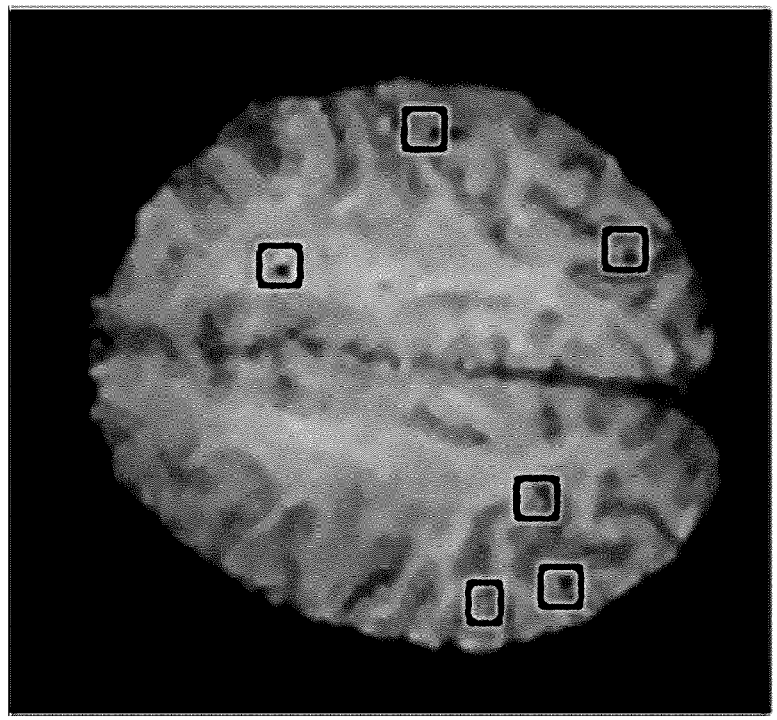
FIG. 5 is a diagram illustrating a candidate region selected through the YOLO neural network module according to the embodiment of the present disclosure.

FIG. 5 is a diagram illustrating the candidate region selected through the YOLO neural network module according to the embodiment of the present disclosure.

The candidate region exemplarily illustrated in FIG. 5 is determined based on the bounding box illustrated in FIG. 4 and the probability information of each bounding box. The probability for selecting as a candidate region may be determined in advance, and a bounding box region exceeding a predetermined probability among a plurality of bounding box regions is selected as the candidate region.

The operation of selecting the candidate region from the output image of the YOLO neural network module may be performed by a separate selection module, and the YOLO neural network module may be trained to select the candidate region with a predetermined probability or more.

Figure 6:
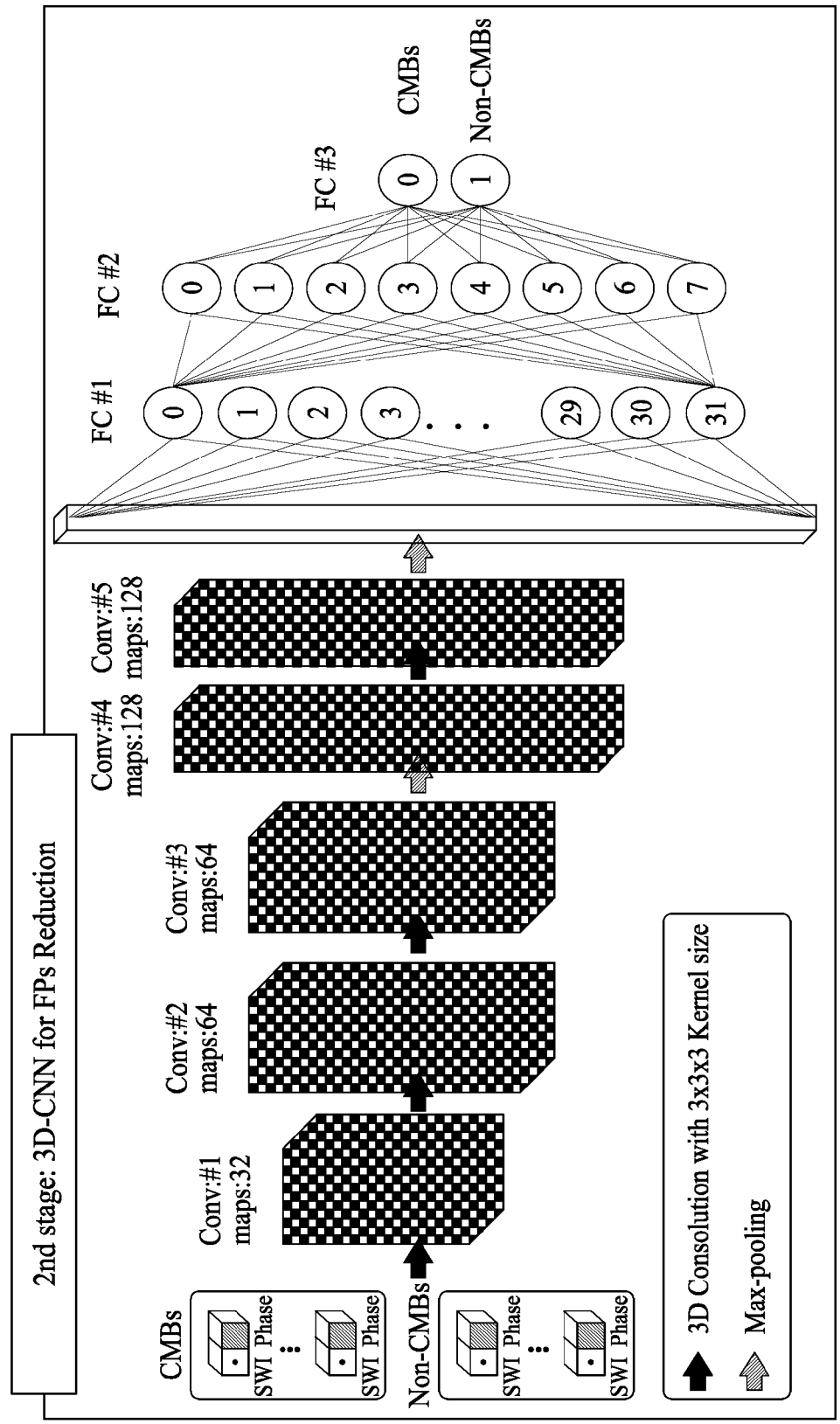
FIG. 6 is a diagram illustrating a structure of a cerebral microbleeds determination neural network module according to an embodiment of the present disclosure.

FIG. 6 is a diagram illustrating the structure of the cerebral microbleeds determination neural network module according to the embodiment of the present disclosure.

When the cerebral microbleeds candidate region is selected using the YOLO neural network module, the patch image of the region is input to the cerebral microbleeds determination neural network module. The patch image of the candidate region is selected from the SWI image and the phase image, respectively, based on the candidate region.

The input image of the YOLO neural network module 200 is an image in which the SWI image and the phase image are concatenated into two channels. The input image of the cerebral microbleeds determination neural network module 300 has a form in which patch images of two selected candidate regions are continuously connected. That is, the input image of the cerebral microbleeds determination neural network module 300 is a one-channel image, and it is preferable that the input image is not a two-channel image like the YOLO neural network module 200.

As described above, the patch image of the candidate region to the cerebral microbleeds determination neural network module may be selected from the input image (preprocessed image) of the YOLO neural network module 200, or may be selected from the image preprocessed in another way.

According to the research of the inventor of the present invention, there is a better training effect and improved detection performance when preprocessed in a manner different from that of the input image to the YOLO neural network module 200.

In this case, the preprocessing unit 100 generates a first preprocessed image for the YOLO neural network module 200 and a second preprocessed image for the cerebral microbleeds determination neural network module 300, respectively.

The second preprocessed image is an image in which no image conversion has been performed on the phase image when compared to the first preprocessed image. In the second preprocessing, the normalization, and the slice average of the SWI image are performed in the same manner. Even for the phase image, the normalization and the slice average are performed, but the phase image conversion is not performed. That is, only the normalization and the slice average are performed on the phase image as in the SWI image.

The reason why the phase image is not converted is because the input to the cerebral microbleeds determination neural network module 300 is the form in which the two images are continuously connected, not the form in which the two images are concatenated.

The cerebral microbleeds determination neural network module 300 includes a plurality of convolutional layers and a plurality of fully connected (FC) layers. Although five convolutional layers and three fully connected (FC) layers are illustrated in FIG. 6, it will be apparent to those skilled in the art that the number of convolutional layers and FC layers can be appropriately selected.

In the convolution layer, the convolution operation using the convolution kernel is performed, and the size and channel may be changed while the convolution operation is performed. In the FC layer, the operation is performed to reduce the class of the operation result of the convolution layer, and finally only two classes are output.

The cerebral microbleeds determination neural network module 300 is trained to finally determine whether the input patch image of the candidate region (the image in which the SWI image and the phase image are connected) is an image with symptoms of the cerebral microbleeds (CMBs). For example, the training may be made so that in the case of the image with the symptoms of the cerebral microbleeds, a value close to 0 may be output, and in the case of the image having no symptoms of the cerebral microbleeds, a value close to 1 may be output.

The cerebral microbleeds determination neural network module 300 may also be trained using the ground truth (GT). The training is made in a manner that the difference between the output of the cerebral microbleeds determination neural network module 300 and the preset class value (for example, '0' for the cerebral microbleeds image and '1' for noncerebral microbleeds image) is set as a loss and the loss is backpropagated.

The patch images of each of the plurality of candidate regions are input to the cerebral microbleeds determination neural network module 300, and are finally determined whether or not they are the cerebral microbleeds images for the patch images of each candidate region.

FIG. 7 is a flowchart illustrating the overall flow of a method of determining cerebral microbleeds according to an embodiment of the present disclosure.

Referring to FIG. 7, the SWI image and the phase image are prepared respectively (step 700).

The first preprocessing is performed on the SWI image and the phase image (step 702). As described above, the normalization and the slice average operation are performed on the SWI image, and the normalization, the image conversion, and the slice average operations are performed on the phase image.

When the first preprocessing is performed, the preprocessed SWI image and the phase image are concatenated and input to the trained YOLO neural network module 200 to output the cerebral microbleeds candidate region (step 704). The YOLO neural network module 200 outputs the bounding box and the image including the probability information of the bounding box, and outputs the candidate region based on the probability information of each bounding box.

When the candidate region is selected from the SWI image and the phase image, the patch image reflecting the second preprocessing is generated for the candidate region (step 706). As described above, in the second preprocessing, a separate image conversion is not performed on the phase image. The patch image of the candidate region may be an image in which the SWI image and the phase image of the candidate region are continuously connected.

When the patch images of the candidate region are generated, it is determined whether the patch images of each candidate region are images with the symptoms of the cerebral microbleeds using the cerebral microbleeds determination network (step 708).

It can be understood that the above description of the disclosure is for illustrative purposes only, and those skilled in the art to which the disclosure belongs can easily convert the disclosure into another specific form without changing the technical ideas or essential features of the disclosure.

Therefore, it should be understood that the above-mentioned embodiments are exemplary in all aspects but are not limited thereto.

For example, each component described as a single type may be implemented in a distributed manner, and similarly, components described as distributed may be implemented in a combined form.

It is to be understood that the scope of the present disclosure will be defined by the claims rather than the above-mentioned description and all modifications and alternations derived from the claims and their equivalents are included in the scope of the present disclosure.

What is claimed is:

1. A device for detecting cerebral microbleeds using magnetic resonance images, comprising:
   a preprocessing unit that normalizes a sensitivity-weighted imaging (SWI) image and a phase image, respectively, of the magnetic resonance images, and performs phase image conversion for inverting a code of the normalized phase image;
   a You Only Look Once (YOLO) neural network module that receives a two-channel image in which the preprocessed SWI image and phase image are concatenated and detects a plurality of candidate regions for the cerebral microbleeds; and
   a cerebral microbleeds determination neural network module that receives patch images of the candidate regions of the SWI image and phase image based on the plurality of candidate regions and determines whether the patch images of each candidate region are an image with a symptom of the cerebral microbleeds through a neural network operation.

2. The device of claim 1, wherein the preprocessing unit further performs preprocessing of calculating an average value of slice images adjacent to the normalized SWI image and the converted phase image.

3. The device of claim 2, wherein each patch image of the candidate regions for the plurality of candidate regions is generated using a candidate region of the SWI image in which the normalization and the adjacent slice average operation have been performed.

4. The device of claim 3, wherein the each patch image of the candidate regions is a one-channel image in which a portion of the candidate region of the SWI image in which the normalization and the adjacent slice average operation are performed and a portion of the candidate region of the phase image in which the normalization and the adjacent slice average operation are performed are continuously connected.

5. The device of claim 1, wherein the YOLO neural network module is trained by backpropagating a loss with a ground truth (GT) image to output a plurality of bounding boxes and probability information of each bounding box.

6. The device of claim 1, wherein the cerebral microbleeds determination neural network module includes a convolutional neural network (CNN) layer and a fully connected (FC) layer, and is trained by backpropagating a loss with a ground truth (GT).

7. A method of detecting cerebral microbleeds using magnetic resonance images, comprising:
   (a) performing, by a preprocessing unit, preprocessing that normalizes a sensitivity-weighted imaging (SWI) image and a phase image, respectively, of the magnetic resonance images, and performs phase image conversion for inverting a code of the normalized phase image;
   (b) performing, by a You Only Look Once (YOLO) neural network module, a YOLO neural network operation that receives a two-channel image in which the preprocessed SWI image and phase image are concatenated and detects a plurality of candidate regions for the cerebral microbleeds; and
   (c) performing, by a cerebral microbleeds determination neural network module, a cerebral microbleeds determination neural network operation that receives patch images of the candidate regions of the SWI image and phase image based on the plurality of candidate regions and determines whether the patch images of each candidate region are an image with a symptom of the cerebral microbleeds through a neural network operation.

8. The method of claim 7, wherein the preprocessing (a) further performs, by the preprocessing unit, preprocessing of calculating an average value of slice images adjacent to the normalized SWI image and the converted phase image.

9. The method of claim 8, wherein each patch image of the candidate regions for the plurality of candidate regions is generated using a candidate region of the SWI image in which the normalization and an adjacent slice average operation have been performed.

10. The method of claim 9, wherein the each patch image of the candidate regions is a one-channel image in which a portion of the candidate region of the SWI image in which the normalization and the adjacent slice average operation are performed and a portion of the candidate region of the phase image in which the normalization and the adjacent slice average operation are performed are continuously connected.

11. The method of claim 7, wherein in the YOLO neural network operation (b), the YOLO neural network module is trained by backpropagating a loss with a ground truth (GT) image to output a plurality of bounding boxes and probability information of each bounding box.

12. The method of claim 7, wherein in the cerebral microbleeds determination neural network operation (c), the cerebral microbleeds determination neural network module includes a convolutional neural network (CNN) layer and a fully connected (FC) layer, and is trained by backpropagating a loss with a ground truth (GT).

* * * * *